(12) United States Patent
Jurecka et al.

(10) Patent No.: US 10,039,281 B2
(45) Date of Patent: Aug. 7, 2018

(54) PESTICIDAL TAPE FOR CONTROLLING CRAWLING PESTS

(71) Applicant: BASF SE, Ludwigshafen (DE)

(72) Inventors: Peter Jurecka, Mannheim (DE); Eylem Cicek, Stuttgart (DE); Mark Nicolay, Buchs (CH); Jan Metzner, Munich (DE)

(73) Assignee: BASF SE, Ludwigshafen (DE)

( * ) Notice: Subject to any disclaimer, the term of this patent is extended or adjusted under 35 U.S.C. 154(b) by 1 day.

(21) Appl. No.: 15/304,436

(22) PCT Filed: Apr. 16, 2015

(86) PCT No.: PCT/EP2015/058271
§ 371 (c)(1),
(2) Date: Oct. 14, 2016

(87) PCT Pub. No.: WO2015/158826
PCT Pub. Date: Oct. 22, 2015

(65) Prior Publication Data
US 2017/0035047 A1    Feb. 9, 2017
US 2017/0238538 A9    Aug. 24, 2017

(30) Foreign Application Priority Data
Apr. 17, 2014 (EP) .................... 14165211

(51) Int. Cl.
*A01N 25/34*    (2006.01)
*A01N 53/00*    (2006.01)
*A01N 25/10*    (2006.01)
*A01M 1/20*    (2006.01)
*A01M 1/24*    (2006.01)

(52) U.S. Cl.
CPC .......... *A01N 25/34* (2013.01); *A01M 1/2011* (2013.01); *A01M 1/24* (2013.01); *A01N 25/10* (2013.01); *A01N 53/00* (2013.01); *A01M 2200/011* (2013.01)

(58) Field of Classification Search
CPC ........ A01N 53/00; A01N 43/36; A01N 47/02; A01N 25/10; A01N 25/34; A01M 1/2011; A01M 1/24; A01M 2200/011

USPC ......................................................... 424/409
See application file for complete search history.

(56) References Cited

U.S. PATENT DOCUMENTS

| | | | |
|---|---|---|---|
| 3,295,246 A | 1/1967 | Landsman et al. | |
| 3,816,956 A | 6/1974 | Sekula | |
| 2003/0186604 A1* | 10/2003 | Nourigat | A01M 1/04 442/123 |
| 2011/0256195 A1* | 10/2011 | Heinemann | A01N 53/00 424/403 |
| 2012/0114726 A1* | 5/2012 | Leininger | A01N 25/10 424/411 |
| 2012/0291336 A1 | 11/2012 | Friend | |

FOREIGN PATENT DOCUMENTS

| | | | |
|---|---|---|---|
| WO | 02/46503 A1 | 6/2002 | |
| WO | 02/055775 A1 | 7/2002 | |
| WO | 2005064072 A2 | 7/2005 | |
| WO | 2006128870 A2 | 12/2006 | |
| WO | 2007077101 A1 | 7/2007 | |
| WO | 2008052913 A1 | 5/2008 | |
| WO | 2008063540 A1 | 5/2008 | |
| WO | WO 2008063540 A1 * | 5/2008 | .......... A01M 1/2011 |
| WO | 2011003845 A2 | 1/2011 | |
| WO | 2013130452 A1 | 9/2013 | |

OTHER PUBLICATIONS

International Search Report for PCT/EP2015/058271 dated May 27, 2015; 3 Pages.

* cited by examiner

*Primary Examiner* — Johann R Richter
*Assistant Examiner* — Courtney A Brown
(74) *Attorney, Agent, or Firm* — Armstrong Teasdale LLP

(57) ABSTRACT

In a tape for controlling crawling pests, on the first side (S1) is a carrier layer having a multitude of vertically extending structures, and on the opposite side (S2) is a means for attaching the tape to a surface. At least the first side (S1) is impregnated with a composition of A) 0.1 to 45% by weight (based on the total of A plus B) of one or more insecticides and B) 99.9 to 55% by weight (based on the total of A plus B) of an (meth)acrylate binder of one or more homo- or copolymer having units derived from one or more acrylates and/or methacrylates.

10 Claims, No Drawings

PESTICIDAL TAPE FOR CONTROLLING CRAWLING PESTS

CROSS-REFERENCE TO RELATED APPLICATIONS

This application is a U.S. National Phase Application of PCT/EP2015/058271, filed Apr. 16, 2015, which is incorporated herein by reference in its entirety.

DESCRIPTION

The invention relates to a pesticidal tape for controlling crawling pests, in particular bed bugs.

The invention also relates to a method for producing the pesticidal tape for controlling crawling pests and to a method for controlling crawling pests comprising the placement of such a tape.

Crawling pests such as bedbugs (*Cimex lectularius*) can be a nuisance and some biting or blood feeding insects can even transmit infectious diseases. This is not only a problem in tropical countries. Bedbugs, for example, live all over the world with their populations increasing even in the developed world. Bedbugs are blood feeding insects and their name is derived from their preference of living in warm houses and especially nearby or inside of beds. Bed bugs are commonly active between midnight and 5 a.m. and find humans based on body temperatures and carbon dioxide emitted while breathing. Their bites cause itching with the possibility of skin irritation and secondary infection.

US 2012/0291336 A1 discloses a bedbug protective device that combines a bedbug repellent or insecticide with a mechanism for trapping bedbugs. The device comprises flexible carrier strip of a material which is impregnated with a bedbug repellent. The carrier is "V" or "C" shaped with an opening constructed so that bedbugs can easily enter the device. The inside is coated with glue which remains sticky and can trap bedbugs. The backside of the carrier is provided with an adhesive strip with which the device can be attached to bed frames, beds and other furniture.

WO 02/055775 A1 is related to a method for controlling insects. The method comprises placing a fibrous material with a high surface area in contact with a location where invasion by insects is suspected. In one embodiment the material has a dense loop-and-rib weave; in another embodiment terry cloth is used. Insects crawling over the material get caught in the structures of the material. In further embodiments an insecticide can be added to the fibrous material.

U.S. Pat. No. 3,295,246 discloses a tape for controlling crawling insects comprising insecticides, e.g. pyrethroids.

WO 2008/063540 discloses a tape for controlling crawling insects comprising pyrethroids such as permethrin and cypermethrin. The tape has a structured top surface in the form of a web.

WO 2011/003845 discloses an insecticidal coating composition for coating a substitute, especially a net, which comprises a pyrethroid insecticide and chlorfenapyr incorporated into a (meth)acrylate binder.

D. J. Moore et al., Pest Management Science 65 (2009) 332-338, discloses pyrethroids and chlorfenapyr to be effective in combating bed bugs.

WO 2013/130452 discloses a microfabricated surface comprising hooks and loops for capturing insects.

Although the known devices are useful, there is still a strong need for methods and devices for controlling crawling pests, in particular bedbugs, which are effective, easy to use, environmentally friendly and discrete.

It is an object of the present invention to provide means and methods for controlling crawling pests which meet the above requirements.

Accordingly, in one aspect of the invention there is provided a tape for controlling crawling pests, comprising on the first side (S1) a carrier layer, comprising a multitude of vertically extending structures, and on the opposite side (S2) means for attaching the tape to a surface, wherein at least the first side (S1) is impregnated with with a composition comprising A) 0.1 to 45% by weight (based on the total of A plus B) of one or more insecticides and B) 99.9 to 55% by weight (based on the total of A plus B) of an (meth)acrylate binder comprising, preferably consisting of, one or more, preferably one, homo- or copolymer, preferably copolymer, comprising units derived from one or more acrylates and/or methacrylates.

The invention further provides the use of the tape according to the invention for controlling crawling pests, and for protecting humans and domestic animals from crawling pests.

The invention likewise provides methods of protecting humans and domestic animals in a building from crawling pests wherein a tape according to the invention is placed in the building.

The invention further provides a method of producing the tape of the invention, comprising the steps of a) providing a tape comprising a first side (S1) which is a carrier layer, comprising a multitude of vertically extending structures, and an opposite side (S2) comprising attachment means for attaching the tape to a surface, and b) impregnating at least the first side (S1) with a composition comprising A) 0.1 to 45% by weight (based on the total of A plus B) of one or more insecticides and B) 99.9 to 55% by weight (based on the total of A plus B) of a (meth)acrylate binder according to the invention.

The tapes according to the invention are distinguished by simple production and simple application. Tapes according to the invention have a good pesticidal activity and permit an effective protection of humans and domestic animals from crawling pests.

Tape

The pesticidal for controlling crawling pests according to the invention comprises on the first side (S1) a carrier layer, comprising a multitude of vertically extending structures, and on the opposite side (S2) attachment means for attaching the tape to a surface, wherein at least the first side (S1) is impregnated with a composition of the invention.

The base material of the tape, providing a substrate to which the vertically extending structures are attached, may be any flexible material such as polyester, polyamide, or may be formed from the same material as the vertically extending structures.

The vertically extending structures serve to impede and slow down the progress of crawling pests entering the tape, and to increase the exposure of the insect to the pesticidal impregnation. Preferably, the concentration of the insecticide is sufficiently high to kill the insect.

Preferred is a material with vertically extending structures which is capable of restricting the movement of crawling pests of a length of about 0.05-7.5 cm, more preferably about 0.1-2.5 cm.

In a preferred embodiment the vertically extending structures comprise or consist of a fibrous material, preferably a textile material, typically produced from synthetic fibers made e.g. from polyesters, polyamides or polyolefins.

In a preferred embodiment substrate and vertically extending structures are components of hook and loop fasteners (often generically termed Velcro®). Such hook and loop fasteners typically consist of two woven strips of synthetic fibers where one strip comprises flexible hooks and the other one loops. Both types of strips, the ones with the hooks and the ones with the loops may be used according to the invention. In one preferred embodiment, the vertically extending structures are formed by the hooks of a hook and loop fastener. In another preferred embodiment, the vertically extending structures are formed by the loops of a hook and loop fastener.

Preferably, the strips with either hooks or loops are made of polyesters, polyamides or polyolefins, in some cases polyaramides are used.

Such components of hook and loop fasteners are commercially available.

The strips with the hooks or loops can be coated with adhesives on the opposite side (S2) as means to attach the tape of the invention to a surface. Before use, the adhesive layer is typically protected by a removable layer, such as silicon paper.

In another embodiment of the invention a fibrous material as disclosed in WO 02/055775 is used to create the vertically extending structures.

In this embodiment, fibrous materials made from textile fibers are preferred. Particularly preferred are fibrous materials of the soft furnishings or household textile types. These materials are fabrics used in households, hotels, motels, restaurants, Offices, stores, recreational facilities or hospitals. Examples of such woven fabrics or fibrous materials include pile weave fabrics, which have a ground fabric with an extra set of yarns woven or tied into the ground fabric, and projecting from it as cut ends or loops on one or both sides of the ground fabric. An example of a suitable fibrous material is terry cloth, which is a type of cloth covered on both sides with uncut loops of fabric. One set of filling yarn is interwoven with two sets of warp yarn, one of which is held tight and the other is left loose, forming the loops. Remnants of such materials are also useful.

Also preferred are soft fabric materials or cloth made of micro fibers. Preferred micro fiber products will have at least about 10 micro fiber loops per $cm^2$, more preferably about 20-200 micro fiber loops per $cm^2$, most preferably about 40-95 micro fiber loops per $cm^2$. These micro fibers usually extend about 0.1-0.2 to 0.6-0.7 cm above the surface of the carrier layer.

In a further embodiment of the invention a randomly disposed crimped or looped synthetic fibers are used which are bonded together at points where they touch and cross. Such a material is disclosed e.g. in U.S. Pat. No. 4,103,450.

The material may be formed of any filament-forming synthetic polymeric material such as polyester (preferably polyethylene terephthalate), nylon, polyvinyl chloride, polyacrylate and the like. The adhesively bonded material is generally formed of crimped, staple fibers by well-known techniques. The fibers may be bonded together with any one of a variety of well-known adhesive binder materials. The adhesive binder may be either a thermosetting binder or a thermoplastic binder. The binder, of course, should be selected to be compatible with the particular substance forming the fibers and with the particular insecticide material being utilized. Binders which have been found to be particularly suitable for use in bonding the fibers together include phenol-aldehyde resins, butylated urea aldehyde resins, epoxide resins, polyurethane resins, and polyester resins. The amount of binder employed to adhere the fibers together will be the minimum consistent with bonding the fibers together at their points of contact to provide an integral self-supporting three-dimensional structure.

In yet a further embodiment of the invention the vertically extending structures are lamellae formed from typical polymeric materials.

The means for attaching the tape of the invention to a surface are in no way limited and include e.g. adhesives, which can be protected before use by a protective layer such as silicon paper. In one embodiment the means for attaching the tape of the invention to a surface are the hook or loop strip of a hook and loop fastener. In this case the complementary strip of the hook and loop fastener is applied to the surface to which the tape of the invention is attached.

Insecticides

According to the invention, at least one side, S1, of the tape is impregnated with at least one insecticide. The insecticide used may be, in principle, any insecticide that is active against crawling pests. Depending on the nature of the intended use, the skilled worker will make a suitable selection. It is also possible to use mixtures of a variety of insecticides. Furthermore, it is also possible to use combinations of insecticides with metabolic inhibitors, also known as efficiency boosters, such as, for example, piperonyl butoxide (PBO).

Insecticides which are suitable in the invention are mentioned for example in WO 2005/64072, page 11, line 28 to page 14, line 34. Further examples include N-arylhydrazines as mentioned in WO 2006/128870, page 12, line 1 to page 18, line 37.

Preferred are pyrethroid insecticides such as acrinathrin, allethrin, bioallethrin, barthrin, bifenthrin, bioethanomethrin, cyclethrin, cycloprothrin, cyfluthrin, beta-cyfluthrin, cyhalothrin, gammacyhalothrin, lambda-cyhalothrin, cypermethrin, alpha-cypermethrin, beta-cypermethrin, thetacypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin; pyrethroid ether insecticides such as etofenprox, flufenprox, halfenprox, protrifenbute, silafluofen and natural pyrethroids such as pyrethrin 1 and II, cinerin I and II and jasmolin I and II.

Of those are preferred cypermethrin, alpha-cypermethrin, deltamethrin, permethrin, cyfluthrin, beta-cyfluthrin, cyhalothrin and lambda-cyhalothrin.

Especially preferred are alpha-cypermethrin, deltamethrin and permethrin.

Very especially preferred is alpha-cypermethrin.

Further preferred are fipronil and chlorfenapyr.

Preferred is also the use of a mixture of chlorfenapyr and a pyrethroid, preferably alphacypermethrin. In these cases the mixing ratio chlorfenapyrpyrethroid is, generally, 0.01-100:1, preferably 0.1-10:1, especially preferably 0.1-5:1, in particular 0.5-2:1.

The insecticides mentioned above, pyrethroids in general and the active compounds mentioned in particular are known and are commercially available; alpha-cypermethrin, for example, is commercially available from BASF SE, Ludwigshafen, Germany. The active compounds are described for example in The Pesticide Manual (see above). Further information is also found in H. Mehdorn (Ed.), Encyclopedic Reference of Parasitology, 2nd Ed., Disease Treatment, Therapy, 2001. Also, piperonyl butoxide is described in The Pesticide Manual (see above).

The concentration of the insecticide or mixture of insecticide (such as chlorfenapyr and pyrethroid) in the preferably aqueous formulation which serves for impregnating side S1 of the tape of the invention, is adjusted such that the desired insecticide concentration on the tape will result (the liquid uptake of the substrate being known). In general, the amount of the insecticide(s) in the aqueous formulation is from 0.05 to 1% by weight, preferably from 0.1 to 0.7% by weight (based on the aqueous formulation).

The particle size of the insecticide(s) in the aqueous formulation is generally from 50 nm to 20 μm, preferably 50 nm to 8 μm, especially preferably 50 nm to 4 μm, in particular 50 nm to 500 nm.

In addition to insecticides the tape of the invention may contain one or more attractants, such as pheromones, which will help to attract the crawling pests to the tape and such help to control the population in a given area.

Alternatively, if the tape of the invention is to work mainly as a barrier against passing of the insects, the tape may also contain one or more additional repellents.

Finishing the Tape with Insecticides

The side S1 of the tape with the vertically extending structures is impregnated with a formulation comprising at least one insecticide and at least one (meth)acrylate binder. Preferably the treatment is carried out with an aqueous formulation comprising the at least one insecticide and the at least one (meth)acrylate binder.

(Meth)acrylate Binders

The binder serves to fix the insecticide on the tape. By using the (meth)acrylate binder of the invention, undesired leaching of the insecticide is avoided, while at the same time sufficient insecticide is available to effectively act on an insect crossing the tape.

The term (meth)acrylate binder of the invention means homo- or copolymers, preferably copolymers, comprising units derived from acrylate and/or methacrylate monomers. Suitable binders are disclosed for example in WO 2005/064072 on pages 17 to 24 and WO 2008/052913 on pages 21 to 33.

For example, they may be binders which can be obtained by polymerization of at least one monomer selected from the group consisting of (meth)acrylates, in particular $C_1$- to $C_{12}$-esters of (meth)acrylic acid, and (meth)acrylates having crosslinking groups, and optionally of at least one monomer selected from the group consisting of (meth)acrylic acid, (meth)acrylamides, maleic acid, maleic acid esters, acrylonitrile, styrene, vinyl acetate, vinyl alcohol, ethylene, propylene, allyl alcohol and vinyl chloride.

In a preferred embodiment of the invention, this is a copolymer (1) of ethylenically unsaturated monomers which comprises, as monomers, 50 to 95% by weight of at least one (meth)acrylate (1-A) of the general formula $H_2C=CHR^1-COOR^2$, where $R_1$ is H or methyl and $R^2$ is an aliphatic, linear or branched hydrocarbon radical having 1 to 12 carbon atoms, preferably 2 to 10 carbon atoms. $R^1$ is preferably H. Examples of suitable radicals $R^2$ include in particular methyl, ethyl, n-butyl and 2-ethylhexyl radicals, preferably ethyl, n-butyl and 2-ethylhexyl radicals. Moreover, the copolymer (I) comprises 1 to 20% by weight of (meth)acrylic acid or (meth)acrylic acid derivatives (1-B) with additional functional groups. This may take the form in particular of a (meth)acrylic ester and/or (meth)acrylamides. The functional groups serve to bind the binder to the tapes and can furthermore be used for crosslinking. For example, they may take the form of ω-hydroxyalkyl (meth)acrylic esters, (meth)acrylic esters having epoxy groups such as, for example, glycidyl esters, (meth)acrylamides or derivatives thereof such as, for example, (meth)acrylic acid methylolamide $H_2C=CH(CH_3)-CO-HN-CH_2-OH$. It is also possible to employ further ethylenically unsaturated, preferably monoethylenically unsaturated, monomers (1-C) which differ from (1-A) and (1-B), for example acrylonitrile or styrene. As a rule, the amount of further monomers is from 0 to 30% by weight. Details of the copolymers (1) are described in WO 2008/052913 page 23, line 15 to page 30, line 6.

The abovementioned (meth)acrylic binders can preferably be employed by means of emulsion polymerization. Details in this context are described in WO 2005/064072 page 20, line 20 to page 23, line 15.

More preferred is a (meth)acrylate binder (B), obtainable by emulsion polymerization of B1) 20 to 92.8% by weight (based on B) of one or more (meth)acrylates of the formula (I)

$$H_2C=CR^1-COOR^2 \qquad (I)$$

where
$R^1$ is H or $CH_3$ and
$R^2$ is a linear or branched $C_1$-$C_{12}$-alkyl group;

B2) 1 to 7, preferably 1 to 5, % by weight (based on B) of at least one monomer selected from the group consisting of N-methylolacrylamide, N-methylolmethacrylamide, N,N'-bismethylolmaleic diamide and N,N'-bismethylolfumaric diamide;

B3) 0.2 to 5% by weight (based on B) of at least one monomer selected from the group consisting of acrylic acid, methacrylic acid, vinylsulfonic acid, maleic acid and fumaric acid;

B4) 0 to 5% by weight (based on B) of at least one monomer selected from the groups B4A) monomers of the formula (II) and/or (III),

$$H_2C=CR^3X \qquad (II)$$

$$ZHC=CHZ \qquad (III)$$

where the symbols have the following meanings:
$R^3$ is H or $CH_3$,
X is Z, $-CO-NH-CH_2-NH-CO-CR^3=CH_2$ or $COO-CH_2-CO-CH_2-COOR^4$;
Z is $CONH_2$, $CONH-CH_2-OR^5$, $COO-Y-OH$, CO-glycidyl, CHO or $CO-Y-OH$;
Y is $C_1$-$C_8$-alkylene and
$R^4$, $R^5$ are identical or different and are a linear or branched $C_1$-$C_{10}$-alkyl group;

B4B) allyl acrylate, methallyl acrylate, allyl methacrylate, methallyl methacrylate, diallyl maleate, dimethallyl maleate, allyl fumarate, methallyl fumarate, diallyl phthalate, dimethallyl phthalate, diallyl terephthalate, dimethallyl terephthalate, p-divinylbenzene and ethylene glycol diallyl ether;

B5) 0 to 40% by weight (based on B) of at least one monomer selected from the groups B5A) acrylonitrile, methacrylonitrile, maleonitrile and fumaronitrile and/or B5B) unpolar ethylenically unsaturated monomers other than B1-B4.

The more preferred (meth)acrylate binder employed according to the invention is a copolymer which can be obtained by emulsion polymerization of the components B1 to B4, and optionally B5.

As component B1, one or more, preferably 1, 2 or 3, especially preferably 1, (meth)acrylate(s) of the formula (I)

$$H_2C=CR^1—COOR^2 \qquad (I)$$

is/are employed, where the symbols have the following meanings:

$R^1$ is H or $CH_3$, preferably H, and $R^2$ is $C_1$-$C_{10}$-alkyl, preferably methyl, ethyl, n-propyl, i-propyl, n-butyl, i-butyl, sec-butyl, t-butyl, n-pentyl, sec-pentyl, neopentyl, 1,2-dimethylpropyl, i-amyl, n-hexyl, i-hexyl, n-heptyl, n-octyl, 2-ethylhexyl, n-nonyl or n-decyl, especially preferably methyl, ethyl, n-butyl or 2-ethylhexyl, very especially preferred are ethyl, n-butyl or 2-ethylhexyl.

Preferred as component B1 are methyl acrylate, ethyl acrylate, n-butyl acrylate, 2-ethylhexyl acrylate and methyl methacrylate. Also preferred are butyl acrylate on its own or in admixture with methyl methacrylate or ethyl acrylate. Especially preferred is n-butyl acrylate.

Substances which are employed as component B2 are at least one monomer from the group consisting of N-methylolacrylamide, N-methylolmethacrylamide, N,N'-bismethylolmaleic diamide and N,N'-bismethylolfumaric diamide. Preferred are N-methylolacrylamide and N-methylolmethacrylamide, in particular N-methylolmethacrylamide.

Substances which are employed as component B3 are one or more monomers, preferably one or two monomers selected from the group consisting of acrylic acid, methacrylic acid, vinyl-sulfonic acid, maleic acid and fumaric acid. Preferred are acrylic acid and methacrylic acid; acrylic acid is especially preferred.

Substances which are employed as component B4 are one or more monomers, preferably one or two monomers, selected from groups B4A and/or B4B.

Monomers of group B4A are those of the formula (II) and/or (III)

$$H_2C=CR^3X \qquad (II)$$

$$ZHC=CHZ \qquad (III)$$

where the symbols have the following meanings:

$R^3$ is H or $CH_3$, preferably H;

X is Z, —CO—NH—$CH_2$—NH—CO—$CR^3$=$CH_2$ or COO—$CH_2$—CO—$CH_2$—COOR$^4$, preferably Z;

Z equals $CONH_2$, CONH—$CH_2$—OR$^5$, COO—Y—OH, COO-glycidyl, CHO, CO—Y—OH, preferably $CONH_2$;

Y is $C_1$-$C_8$-alkylene, preferably $C_2$-$C_6$-alkylene, and $R^4$, $R^5$ are identical or different and are a linear or branched $C_1$-$C_{10}$-alkyl group; and (meth)acrylic-modified benzophenones, as described, for example, in EP-A 0 346 734.

Preferred as monomers from group B4A are acetoacetyl acrylate, acetoacetyl methacrylate, acrylamide, methacrylamide, maleic diamide, N-methoxymethylacrylamide, N-n-butoxymethylacrylamide, 3-hydroxypropyl acrylate, 3-hydroxypropyl methacrylate, 4-hydroxybutyl acrylate, 4-hydroxybutyl methacrylate, 6-hydroxyhexyl acrylate, 6-hydroxyhexyl methacrylate, 2-hydroxy-3-chloropropyl acrylate, 3-hydroxy-3-chloropropyl methacrylate, glycidyl acrylate and glycidyl methacrylate. Especially preferred are acrylamide, 3-hydyroxypropyl methacrylate, butanediol monoacrylate acetylacetate, glycidyl methacrylate, and 4-acryloxy-benzophenone.

Substances which are preferably employed as monomers from group B4B are allyl acrylate, methallyl acrylate, allyl methacrylate, methallyl methacrylate, diallyl maleate, dimethylallyl maleate, allyl fumarate, methallyl fumarate, diallyl phthalate, dimethylallyl phthalate, diallyl terephthalate, dimethallyl terephthalate, p-divinylbenzene, butane-1,4-diol diallyl ether and butane-1,4-diol dimethylallyl ether.

Preferred monomers of group B4 are those of group B4A, the use of one or two monomers from among this group being preferred.

Preferred monomers of group B5 are those of group B5A, and also vinylaromatic monomers of group B5B.

It is preferred to employ acrylonitrile or methacrylonitrile, preferably acrylonitrile, as component B5A.

Preferred as component B5B are styrene and a-methylstyrene, styrene being especially preferred.

In a preferred embodiment, acrylonitrile is employed as monomer of component B5 for the preparation of the acrylate binder.

The acrylate binder (B) is obtainable by emulsion polymerization of (data in % by weight are in each case based on the total amount of B):

b1) 20 to 93% by weight, preferably 50 to 90% by weight, especially preferably 60 to 90% by weight, in particular 75 to 85% by weight, of component B1;

b2) 1 to 5% by weight, preferably 1.5 to 3% by weight of component B2;

b3) 0.2 to 5% by weight, preferably 0.5 to 4% by weight, especially preferably 0.75 to 4% by weight, in particular 1 to 3% by weight of component B3;

b4) 0 to 7% by weight, preferably 0 to 5% by weight, especially preferably 0 to 4.5% by weight, in particular 0 or 0.2 to 4.5% by weight of component B4 and b5) 0 to 40% by weight, preferably 5 to 40% by weight, especially preferably 5 to 30% by weight, in particular 0 or 5 to 26% by weight of component B5.

Suitable processes are known to the skilled worker and described, for example, in WO 2005/064072 (page 20, line 20 to page 23, line 15).

The weight-average molecular weight of the non-crosslinked emulsion polymers obtained is generally between 40 000 and 250 000 (as determined by GPC (gel permeation chromatography)). The molecular weight is generally adjusted by using chain termination reagents, for example organosulfur compounds, in the usual amounts.

The (meth)acrylate binder employed according to the invention is generally obtained in the form of an aqueous dispersion and is usually employed in this form in the pesticidal formulation according to the invention.

The acrylate binder according to the invention can furthermore comprise usual additives known to the skilled worker, for example film formers and/or plasticizers, such as adipates, phthalates, butyl diglycol, mixtures of diesters, obtainable by reacting dicarboxylic acids with straight-chain or branched alcohols. Suitable dicarboxylic acids and alcohols are known to the skilled worker.

Formulation for Impregnation—Crosslinker

To prepare the tape according to the invention the (meth)acrylate binders may be employed in the form of a formulation in a solvent, preferably as an aqueous formulation. However, the invention also comprises the use of solvent-free formulations.

In a preferred embodiment, aqueous formulations are employed which comprise 55 to 99% by weight of water, preferably 85 to 98% by weight of water and 0.5 to 45% by weight, preferably 1 to 10% by weight, of solids, the quantities given being in each case based on the total of all components in the formulation. The precise concentration also depends on the adsorptivity of the textile material.

The solids take the form of the (meth)acrylate binder, the insecticide(s), optionally at least one crosslinker and optionally further components.

It is preferred to employ at least one water-dispersible crosslinker. This may in particular take the form of a crosslinker which has free isocyanate groups. These preferably take the form of isocyanurates which have free isocyanate groups, preferably isocyanurates which are derived from aliphatic, cycloaliphatic or aromatic diisocyanates having 4 to 12 carbon atoms. Examples comprise 1,6-hexamethylene diisocyanate (HMDI), 1,12-dodecane diisocyanate, 2,2'- and 2,4'-dicyclohexylmethane diisocyanate, 2,6 and/or 2,4-tolyl diisocyanate, 2-ethyltetramethylene diisocyanate, 2-methylpentamethylene diisocyanate, tetramethylene 1,4-diisocyanate, lysin ester diisocyanate (CD), cyclohexane 1,3- and/or 1,4-diisocyanate, 1-isocyanato-3,3,5-trimethyl-5-isocyanatomethylcyclohexane (IPDI), 4,4'-, 2,4'- and/or 2,2'-diphenylmethanediisocyanate (monomeric MDI), polyphenyl polymethylene polyisocyanate (polymeric MDI) or mixtures comprising at least two of the abovementioned isocyanates. Preferred are isocyanurates based on 1,6-hexamethylene diisocyanate. Especially preferred are isocyanurates which have additional hydrophilic groups such as, in particular, polyethylene oxide groups. Very especially preferred are isocyanates which have been hydrophilicized with a polyalkylene oxide based on ethylene oxide and/or 1,2-propylene oxide, preferably ethylene oxide.

The isocyanurates employed as crosslinkers according to the invention preferably comprise from 5 to 25% by weight, especially preferably from 7 to 20% by weight, in particular from 10 to 15% by weight, of free isocyanate groups (based on the amount of isocyanate which has been employed as starting materials for preparing the isocyanurates).

The preparation of such isocyanurates is known to the skilled worker. They are preferably employed as a solution in polar aprotic solvents such as ethylene carbonate or propylene carbonate. Further details on the preferred crosslinkers having isocyanate groups are disclosed in WO 2008/052913 page 34, line 6 to page 35, line 3. It is especially preferred to employ an isocyanurate which is based on 1,6-hexamethylene diisocyanate (HMDI) and which has additional polyethylene oxide groups, the isocyanurate being dissolved in propylene carbonate (70% by weight of HMDI in propylene carbonate). The free isocyanate groups amount to approximately 11 to 12% by weight based on the solution. The crosslinker is preferably employed in an amount of from 1 to 10% by weight based on the amount of all solids of the formulation.

The formulation may furthermore comprise typical additives and adjuvants, UV stabilizers, defoamers and colorants. Examples of such additives are mentioned in WO 2006/128870 page 41, line 38 to page 43, line 22.

Besides serving purely esthetic purposes, colorants and pigments may have a behavioural effect on the crawling pests. Moreover, dark colors may bring about shading, which may be desired, and may reduce the harmful effect of UV light on active compounds and textile fibers when used in the open.

Crosslinkers and thickeners may be employed to enable uniform impregnation with the treatment liquor of substrates which can only be wetted with difficulty, and therefore inhomogeneously, such as, for example, polyolefin fibers. For this purpose, it would also be possible to employ water-miscible solvents, which, however, is not preferred due to the possible harmful effect on the environment. A person skilled in the art is familiar with the adjuvants which are conventionally used and with their concentrations.

The formulations may preferably comprise antioxidants, peroxide scavengers, UV absorbers and light stabilizers. This is particularly recommended in the case of tapes which are exposed to increased UV irradiation in the open. The abovementioned additives protect not only the tape fibers, but also the active compounds, from decomposition due to radiation.

Suitable UV absorbers are described for example in WO 02/46503 or in WO 2007/077101. The amount in the formulation will be adjusted by the skilled worker to suit the task in hand.

Impregnation Method

To prepare the impregnate tape according to the invention, the tape, or at least side S1 with the vertically extending structures, is treated with a mixture comprising at least the acrylate binder and the insecticide(s), preferably with the abovementioned aqueous formulation. The treatment can be carried out by processes known to the skilled worker, for example by immersing or spraying the untreated tape with the formulation. The treatment can be carried out at room temperature or else at elevated temperatures. If crosslinking is to be carried out, the treatment step at lower temperatures, for example at from 10 to 70° C., may be followed by an aftertreatment at elevated temperatures, for example from 50 to 170° C., preferably from 70 to 150° C. Details of such a treatment are disclosed for example in WO 2005/064072, page 29, line 16 to page 35, line 36.

Impregnation can be effected by means of customary treatment apparatuses known to the skilled worker.

In a preferred embodiment a method for producing a tape according to the invention comprises the steps of
a. providing a carrier layer with a first side (S1) having a multitude of vertically extending structures,
b. applying an impregnant using a two roll padder,
c. drying the carrier layer, and
d. applying an attachment means to the second side opposite to the first surface of the carrier layer,
wherein the impregnant comprises one or more insecticides, the (meth)acrylate binder of the invention and optionally a crosslinker.

Preferably the roll pressure in step b) is between 0.5 to 3 bar. Further preferred the temperature in step c) is between 60 to 90° C.

Properties and use of the Tape According to the Invention

Tapes according to the invention are suitable for protecting humans, domestic animals, stored goods and plants from crawling pests. They are particularly useful for protecting humans from bedbugs.

Tapes according to the invention are also suitable for controlling crawling pests, wherein the tape according to the invention is fixed to a surface in a building. In a preferred embodiment of the method according to the invention, a flexible tape according to the invention is fixed to a surface between a living being or an inanimate object which, being a potential source of food, attracts the crawling pests.

The term crawling pests comprises according to the invention comprises crawling insects and crawling arachnids (*Arachnida*).

For example, the tapes according to the invention are suitable against:

Hemipterans (*Hemiptera*), such as lice, fleas and bugs, for example

Bugs (*Heteropterida*): Cimex lectularius, Cimex hemipterus, Reduvius senilis, Triatoma spp., Rhodnius ssp., Panstrongylus ssp. and Arilus critatus, Fleas (*Siphonaptera*), for example Ctenocephalides felis, Ctenocephalides canis, Xenopsylla cheopis, Pulex irritans, Tunga penetrans and Nosopsyllus fasciatus, Bristletails (*Thysanura*), such as silverfish and firebrats, for example Lepisma saccharina and Thermobia domestica, Lice (*Phthiraptera*), for example *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*;

Ants (*Hymenoptera*), e.g. *Athalia rosae, Atta capiguara, Atta cephalotes, Atta cephalotes, Atta laevigata, Atta robusta, Atta sexdens, Atta texana, Lasius* spp. such as *Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenopsis geminata, Solenopsis invicta, Solenopsis richteri, Solenopsis xyloni,*

Centipedes (*Chilopoda*), e.g. *Geophilus* spp., *Scutigera* spp. such as *Scutigera coleoptrata;*

Millipedes (*Diplopoda*), e.g. *Blaniulus guttulatus, Narceus* spp.,

Spiders (*Araneae*), for example *Latrodectus mactans* and *Loxosceles reclusa,*

Parasitic mites (*Parasitiformes*): ticks (*Ixodida*), for example *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and *Mesostigmata*, for example *Ornithonyssus bacoti* and *Dermanyssus gallinae,*

Termites (*Isoptera*), e.g. *Calotermes flavicollis, Coptotermes formosanus, Heterotermes aureus, Heterotermes longiceps, Heterotermes tenuis, Leucotermes flavipes, Odontotermes* spp., *Reticulitermes* spp. such as *Reticulitermes speratus, Reticulitermes flavipes, Reticulitermes grassei, Reticulitermes lucifugus, Reticulitermes santonensis, Reticulitermes virginicus; Termes natalensis,*

Cockroaches (*Blattaria-Blattodea*), e.g. *Acheta domesticus, Blatta orientalis, Blattella asahinae, Blattella germanica, Gryllotalpa* spp., *Leucophaea maderae, Locusta* spp., *Melanoplus* spp., *Periplaneta americana, Periplaneta australasiae, Periplaneta brunnea, Periplaneta fuliggi-nosa, Periplaneta japonica,*

Earwigs (*Dermaptera*), for example *Forficula auricularia,*

Actinedida (*Prostigmata*) und Acaridida (*Astigmata*) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Anoplurida, e.g. *Haematopinus* spp., *Linognathus* spp., *Pediculus* spp., *Phtirus* spp., and *Solenopotes* spp, Mallophagida (suborders Arnblycerina and lschnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.

Preferred is the use against bugs (*Heteropterida*): e.g. *Cimex lectularius, Cimex hemipterus, Reduvius senilis, Triatoma* spp., *Rhodnius* ssp., *Panstrongylus* ssp. and *Arilus critatus*, in particular against bed bugs (*Cimex lectularius*).

Tapes according to the invention are also suitable for controlling crawling insects which display resistance either to pyrethroids or to chlorfenapyr, preferably pyrethroids.

One preferred application of the tape of the invention is in the protection from bed bugs, e.g. homes and hotels. In these cases, the tape may be used, e.g. in placements around bed legs or the base of a bed. Further, for the control of bed bugs one or more tapes of the invention can be placed around the main spots of the bed bugs' movement in the room. The tape of the invention is suitable for discrete applications, which may be desirable, e.g. in hotel rooms.

For other household applications the tape may be used for blocking the pests' points of entry into the house or their preferred pathways within the house. The tape can also be placed around the bottom of rooms (whole or partially) like the kitchen or food storage rooms. It can also be placed furniture or storage facilities (such as the frames of storage facilities or palettes).

The size and dimensions of the tape of the invention are not critical and can be adapted to the desired applications.

Typically, the width of the tape will be in the range of from 1 to 5 cm, while the length is adapted to the specific application.

In addition, the tapes according to the invention are also suitable for protecting crops to be stored, that is to say harvested plants or plant parts, if appropriate also in processed form.

They can be employed for example by placing the tapes around storage facilities of the goods to be protected. The goods to be protected may, for example, take the form of wood stacks, fruit, vegetables, cereals, cocoa beans, coffee beans, spices, tea, tobacco or cotton.

The invention is illustrated in greater detail by the examples without being limited thereby.

EXAMPLES

A) (Meth)acrylate Binder
Preparation of the Polymer Dispersions
General Procedure 250 g of water and 3 g of styrene seed latex (33% by weight) with a mean particle size of 30 nm are heated to 85° C., whereupon 5% by weight of the feed 2 are added. After 10 min, the addition of feed 1 (see below) and the remainder of feed 2 starts.

Feed 2 comprises 30 g of sodium peroxydisulfate dissolved in 39.9 g of $H_2O$. The composition of feed 1 is shown in table 1. Feeds 1 and 2 are added in the course of 3 hours, followed by afterpolymerization for 0.5 hour.

TABLE 1

Composition of feed 1 in % by weight pphm (parts per hundred monomers)

| Monomer composition | MMA | S | AN | EHA | BA | EA | MaMol | AMol | AM | AS |
|---|---|---|---|---|---|---|---|---|---|---|
| A 1 | | 16.6 | | 30.0 | 30.0 | 20.0 | | 3.0 | | 0.4 |
| A 2 | 25.7 | 5.0 | | 5.3 | 60.0 | | 3.5 | | | 0.5 |
| A 3 | | 14.7 | 11.0 | | 70.0 | | 3.5 | | 0.5 | 0.3 |
| A 4 | 30.0 | 13.0 | 8.0 | | 45.2 | | | 3.0 | 0.5 | 0.3 |
| A 5 | 20.0 | 20.0 | | 17.0 | 23.0 | 15.3 | 3.5 | | | 1.2 |
| A 6 | | 9 | | | 36.9 | 43.4 | | 3.2 | | 1.2 |
| A 7 | 26.0 | | 13.0 | | 57.0 | | 3.0 | | | 1.0 |

TABLE 1-continued

| Composition of feed 1 in % by weight pphm (parts per hundred monomers) | | | | | | | | | | |
|---|---|---|---|---|---|---|---|---|---|---|
| Monomer composition | MMA | S | AN | EHA | BA | EA | MaMol | AMol | AM | AS |
| A 8 | 15.0 | | 13.0 | | 68.0 | | 3.0 | | | 1.0 |
| A 9 | | | 16.0 | | 81.0 | | 2.0 | | | 1.0 |

The amount of the initiator sodium peroxydisulfate is 0.3 parts by weight, that of the emulsifier 0.4 parts by weight of Dowfax 2A1 (Dow) and 0.6 parts by weight of Lumiten IRA (BASF SE), based on 100 parts by weight of the monomer composition of table 1.

Abbreviations
MMA: Methyl methacrylate
S: Styrene
AN: Acrylonitrile
EA: Ethyl acrylate
EHA: 2-Ethylhexyl acrylate
BA: n-Butyl acrylate
Amol: N-Methylolacrylamide
MAMol: N-Methylolmethacrylamide
AS: Acrylic acid
AM: Acrylamide Dowfax 2A1:

Lumiten IRA:

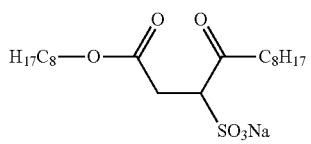

B) Tapes

TABLE 1

Tapes evaluated
The tapes are supplied with a hook and loop material as indicated and are treated with formulations as indicated.

| Tape[1] | Active[2]/rate | Binder[3] | Color/ hook or loop | Tape | Active[2]/rate | Binder[3] | Color/ hook or loop |
|---|---|---|---|---|---|---|---|
| tape 1 | Alpha 200 mg/m² | 0.1% | Black Loop | tape 13 | Alpha 0.25% | 0.5% | Black Loop |
| tape 2 | | 0.1% | White Loop | tape 14 | | 0.5% | White Loop |
| tape 3 | | 0.1% | Black Hook | tape 15 | | 0.5% | Black Hook |
| tape 4 | | 0.1% | White Hook | tape 16 | | 0.5% | White Hook |
| tape 5 | CFP 200 mg/m² | 0.1% | Black Loop | tape 17 | CFP 0.25% | 0.5% | Black Loop |
| tape 6 | | 0.1% | White Loop | tape 18 | | 0.5% | White Loop |
| tape 7 | | 0.1% | Black Hook | tape 19 | | 0.5% | Black Hook |
| tape 8 | | 0.1% | White Hook | tape 20 | | 0.5% | White Hook |
| tape 9 | Alpha 100 mg + | 0.1% | Black Loop | tape 21 | Alpha 0.125% + | 0.5% | Black Loop |
| tape 10 | CFP 100 mg/m² | 0.1% | White Loop | tape 22 | CFP 0.125% | 0.5% | White Loop |
| tape 11 | | 0.1% | Black Hook | tape 23 | | 0.5% | Black Hook |
| tape 12 | | 0.1% | White Hook | tape 24 | | 0.5% | White Hook |
| Untreated | | | Black Loop White Loop | Untreated | | | Black Hook White Hook |

[1]Samples 1-12 supplied with adhesive backing attached.
[2]Alpha = alpha-cypermethrin, CFP = chlorfenapyr.
[3]Based on binder A6
Tapes provided with active ingredient rates as shown.

Methods

Wooden dowel rods (2.4 cm dia) were cut to 10 cm lengths. Treated hook and loop strips, 2 cm wide, were cut to length (7.5 cm) and wrapped around the rods, one each, 6 cm from one end. Tapes 1-12 were secured by adhesive backing on the strips. Tapes 13-24 did not have adhesive backing and so were secured with hot glue. After securing the strips, hot glue was applied to the end of the dowel farthest from the strip and secured vertically to a 10 cm plastic Petri dish or lid. The dowel was marked 3 cm from the dish/lid as the introduction point for bed bugs. For evaluations, one adult bed bug was placed on the marked release point on the dowel and a timer started. Time to reach and cross (exposure time to the treatments) the strip was recorded. Cases in which the insect mounted and subsequently left the strip without crossing were noted and the total time on the strip recorded upon final crossing. Insects that would mount but not cross the strip after an extended period of time were removed and the time on the strip recorded. Three replicates of six individual bed bugs (18 total insects per treatment) of the 24 treated samples were conducted. After exposure, each insect was held individually in six-well cell culture plates, one piece of filter paper per well, for observation. Mortality was evaluated at 1, 2, 3, 6, and 9 days post exposure.

Results

Tape crossing events (Table 2)

TABLE 2

Bed bug crossing data for pesticidal treated hook and loop tapes affixed to vertical wooden dowels

| Tape | Active[1]/rate | Binder[3] | Color/ hook or loop [2] | Time on strip (sec) | Mediän | Number of insects never crossing strip [4] | Number of insects with multiple mounts |
|---|---|---|---|---|---|---|---|
| tape 1 | Alpha | 0.1% | B/L | 36.2 | 16.5 | 4 | 3 |
| tape 2 | 200 mg/m2 | 0.1% | W/L | 18.1 | 12.5 | 0 | 2 |
| tape 3 | | 0.1% | B/H | 36.2 | 33.5 | 6 | 8 |
| tape 4 | | 0.1% | W/H | 33.7 | 35.0 | 9 | 7 |
| tape 5 | CFP | 0.1% | B/L | 13.1 | 7.0 | 1 | 1 |
| tape 6 | 200 mg/m2 | 0.1% | W/L | 14.3 | 9.0 | 1 | 1 |
| tape 7 | | 0.1% | B/H | 32.9 | 22.5 | 5 | 5 |
| tape 8 | | 0.1% | W/H | 30.3 | 23.0 | 2 | 2 |
| tape 9 | | 0.1% | B/L | 30.9 | 17.5 | 5 | 2 |
| tape 10 | | 0.1% | W/L | 13.3 | 10.5 | 3 | 2 |
| tape 11 | | 0.1% | B/H | 32.4 | 24.0 | 9 | 5 |
| tape 12 | | 0.1% | W/H | 27.8 | 22.0 | 7 | 6 |
| tape 13 | | 0.5% | B/L | 12.8 | 8.0 | 0 | 5 |
| tape 14 | | 0.5% | W/L | 11.4 | 9.5 | 0 | 6 |
| tape 15 | | 0.5% | B/H | 16.3 | 10.0 | 0 | 3 |
| tape 16 | | 0.5% | W/H | 17.7 | 13.0 | 0 | 3 |
| tape 17 | | 0.5% | B/L | 12.8 | 8.0 | 0 | 1 |
| tape 18 | | 0.5% | W/L | 10.4 | 7.5 | 0 | 2 |
| tape 19 | | 0.5% | B/H | 18.4 | 10.5 | 0 | 3 |
| tape 20 | | 0.5% | W/H | 17.9 | 17.5 | 0 | 4 |
| tape 21 | | 0.5% | B/L | 11.3 | 9.0 | 0 | 1 |
| tape 22 | | 0.5% | W/L | 14.8 | 8.5 | 0 | 3 |
| tape 23 | | 0.5% | B/H | 18.4 | 13.5 | 0 | 0 |
| tape 24 | | 0.5% | W/H | 22.5 | 15.5 | 0 | 5 |
| Unt BL | | | B/L | 28.5 | 23.0 | 0 | 1 |
| Unt WL | | | W/L | 11.6 | 9.0 | 0 | 2 |
| Unt BH | | | B/H | 38.2 | 31.5 | 11 | 2 |
| Unt WH | | | W/H | 32.6 | 30.0 | 6 | 8 |

[1] Alpha = alpha-cypermethrin, CFP = chlorfenapyr.

Treatments provided with active ingredient rates as shown.

Samples 1-12 were provided with adhesive strips, no adhesive on samples 13-24.

[2] B = black, W = white, L = loop side, H = hook side.

3 Based on binder A6

[4] Bed bug exposures replicated three times, six individual bed bugs per replicate (18 total insects).

Untreated hook tapes were the most difficult for bed bugs to cross. This may be due to the deformation of hooks during treatment resulting in slightly flattened hooks relative to untreated tapes.

Mortality (Table 3)

TABLE 3

Bed bug mortality data from contacting/crossing insecticide treated hook and loop tapes affixed to vertical wooden dowels

| Tape | Active/rate[1] | Binder[3] | Color/hook or loop [2] | Mean % dead at: [4] | | | |
|---|---|---|---|---|---|---|---|
| | | | | 2 d | 3 d | 6 d | 9 d |
| tape 1 | Alpha | 0.10% | B/L | 44.4 | 55.6 | 55.6 | 55.6 | 72.2 |
| tape 2 | 200 mg/m2 | 0.10% | W/L | 16.7 | 27.8 | 44.4 | 44.4 | 66.7 |
| tape 3 | | 0.10% | B/H | 11.1 | 16.7 | 22.2 | 50.0 | 66.7 |
| tape 4 | | 0.10% | W/H | 11.1 | 33.3 | 50.0 | 66.7 | 83.3 |
| tape 5 | CFP | 0.10% | B/L | 0.0 | 0.0 | 0.0 | 22.2 | 61.1 |
| tape 6 | 200 mg/m2 | 0.10% | W/L | 0.0 | 0.0 | 0.0 | 0.0 | 44.4 |
| tape 7 | | 0.10% | B/H | 0.0 | 5.6 | 5.6 | 27.8 | 27.8 |
| tape 8 | | 0.10% | W/H | 0.0 | 0.0 | 0.0 | 11.1 | 27.8 |
| tape 9 | Alpha | 0.10% | B/L | 5.6 | 11.1 | 22.2 | 33.3 | 55.6 |
| tape 10 | 100 mg + CFP | 0.10% | W/L | 11.1 | 16.7 | 22.2 | 44.4 | 61.1 |
| tape 11 | 100 mg/m2 | 0.10% | B/H | 0.0 | 11.1 | 16.7 | 27.8 | 61.1 |
| tape 12 | | 0.10% | W/H | 5.6 | 5.6 | 5.6 | 27.8 | 50.0 |
| tape 13 | | 0.50% | B/L | 22.2 | 22.2 | 50.0 | 83.3 | 83.3 |
| tape 14 | | 0.50% | W/L | 16.7 | 22.2 | 27.8 | 50.0 | 72.2 |
| tape 15 | | 0.50% | B/H | 11.1 | 22.2 | 22.2 | 38.9 | 44.4 |
| tape 16 | | 0.50% | W/H | 11.1 | 22.2 | 33.3 | 44.4 | 66.7 |
| tape 17 | | 0.50% | B/L | 5.6 | 11.1 | 16.7 | 33.3 | 44.4 |
| tape 18 | | 0.50% | W/L | 0.0 | 0.0 | 5.6 | 22.2 | 27.8 |
| tape 19 | | 0.50% | B/H | 0.0 | 0.0 | 5.6 | 11.1 | 16.7 |
| tape 20 | | 0.50% | W/H | 0.0 | 0.0 | 0.0 | 0.0 | 5.6 |
| tape 21 | | 0.50% | B/L | 0.0 | 0.0 | 11.1 | 27.8 | 38.9 |
| tape 22 | | 0.50% | W/L | 11.1 | 16.7 | 22.2 | 44.4 | 50.0 |
| tape 23 | | 0.50% | B/H | 0.0 | 11.1 | 16.7 | 22.2 | 33.3 |
| tape 24 | | 0.50% | W/H | 5.6 | 11.1 | 11.1 | 27.8 | 38.9 |
| Unt BL | | | B/L | 0.0 | 0.0 | 0.0 | 16.7 | 38.9 |
| Unt WL | | | W/L | 0.0 | 0.0 | 0.0 | 5.6 | 11.1 |
| Unt BH | | | B/H | 0.0 | 5.6 | 5.6 | 16.7 | 44.4 |
| Unt WH | | | W/H | 5.6 | 5.6 | 11.1 | 16.7 | 16.7 |

[1] Alpha = alpha-cypermethrin, CFP = chlorfenapyr.
Tapes provided with active ingredient rates as shown.
Tapes 1-12 were provided with adhesive strips, no adhesive on samples 13-24.
[2] B = black, W = white, L = loop side, H = hook side.
[3] Based on binder A6
[4] Bed bug exposures replicated three times, six individual bed bugs per replicate (18 total insects).

Treatments of alpha-cypermethrin alone provided the longest bed bug exposures to treatment (longest time to cross) and the highest mortality, ranging from 39-83%.

The invention claimed is:

1. A tape for controlling crawling pests, comprising on the first side (S1) a carrier layer, comprising a multitude of vertically extending structures, and on the opposite side (S1) means for attaching the tape to a surface,
    wherein at least the first side (S1) is impregnated with a composition comprising
    A) 0.1 to 45% by weight (based on the total of A plus B) of one or more insecticides and
    B) 99.9 to 55% by weight (based on the total of A plus B) of a (meth)acrylate binder comprising one or more homo or copolymer, comprising units derived from one or more acrylates and/or methacrylates.

2. The tape of claim 1 characterized in that the carrier layer is a hook and loop strip and the vertically extending structures are hooks or loops.

3. The tape of claim 1, characterized in that the attachment means comprises a sticky layer and a cover layer wherein the sticky layer is attached to the second surface of the carrier layer with a first surface of the sticky layer and the cover layer is attached to a second surface of the sticky layer opposite to the first surface of the sticky layer.

4. The tape of claim 1 characterized in that the insecticide is selected from pyrethroids, chlorfenapyr, fipronil or a mixture of two of those insecticides.

5. The tape of claim 4 characterized in that the insecticide is alpha-cypermethrin.

6. The tape of claim 1 characterized in that the (meth) acrylate binder (B) is obtainable by emulsion polymerization of B1) 20 to 93% by weight (based on B) of one or more (meth)acrylates of the formula (I)

$$H_2C=CR^1-COOR^2 \qquad (I)$$

where

R1 is H or CH3 and

R2 is a linear or branched C1-C12-alkyl group;

B2) 1 to 5% by weight (based on B) of at least one monomer selected from the group consisting of N-methylolacrylamide, N-methylolmethacrylamide, N,N'-bismethylolmaleic diamide and N,N'-bismethylolfumaric diamide;

B3) 0.2 to 5% by weight (based on B) of at least one monomer selected from the group consisting of acrylic acid, methacrylic acid, vinylsulfonic acid, maleic acid and fumaric acid;

B4) 0 to 5% by weight (based on B) of at least one monomer selected from the groups B4A) monomers of the formula (II) and/or (III), $$H_2C=CR^3X \quad (II)$$

$$ZHC=CHZ \quad (III)$$

where the symbols have the following meanings:
R3 is H or CH3,
X is Z, —CO—NH—CH2-NH—CO—CR3=CH2 or COO—CH2-CO—CH2-COOR4;
Z is CONH2, CONH—CH2-OR5, COO—Y—OH, CO-glycidyl, CHO or CO—Y—OH;
Y is C1-C8-alkylene and
R4, R5 are identical or different and are a linear or branched C1-C10-alkyl group;
B4B) allyl acrylate, methallyl acrylate, allyl methacrylate, methallyl methacrylate, diallyl maleate, dimethallyl maleate, allyl fumarate, methallyl fumarate, diallyl phthalate, dimethallyl phthalate, diallyl terephthalate, dimethallyl terephthalate, p-divinylbenzene and ethylene glycol diallyl ether;
B5) 0 to 40% by weight (based on B) of at least one monomer selected from the groups
B5A) acrylonitrile, methacrylonitrile, maleonitrile and fumaronitrile and/or
B5B) unpolar ethylenically unsaturated monomers other than B1-B4.

7. The tape of claim 1 characterized in that the (meth)acrylate binder has been crosslinked with a crosslinker which has free isocyanate groups.

8. A method for controlling crawling pests comprising the placement of a tape according to claim 1 at the perimeter of an area to be protected.

9. A method of protecting humans and domestic animals in a building from crawling pests characterized in that a tape according to claim 1 is placed in the building.

10. A method of producing a tape according to claim 1, comprising the steps of
   a) providing a tape comprising a first side (S1) which is a carrier layer, comprising a multitude of vertically extending structures, and an opposite side (S1) comprising attachment means for attaching the tape to a surface, and
   b) impregnating the first side (S1) with a composition comprising
      A) 0.1 to 45% by weight (based on the total of A plus B) of one or more insecticides and
      B) 99.9 to 55% by weight (based on the total of A plus B) of a (meth)acrylate binder according to the invention.

* * * * *